(12) United States Patent
Das et al.

(10) Patent No.: US 7,638,309 B2
(45) Date of Patent: Dec. 29, 2009

(54) METHOD FOR DETECTING PATHOGENIC MYCOBACTERIA IN CLINICAL SPECIMENS

(75) Inventors: Rakha Hari Das, New Delhi (IN); Ajay Kumar, New Delhi (IN); Meghpati Singh, New Delhi (JP)

(73) Assignee: Council of Science and Industrial Research, New Delhi (IN)

( * ) Notice: Subject to any disclaimer, the term of this patent is extended or adjusted under 35 U.S.C. 154(b) by 581 days.

(21) Appl. No.: 10/725,994

(22) Filed: Dec. 3, 2003

(65) Prior Publication Data
US 2005/0123928 A1    Jun. 9, 2005

(51) Int. Cl.
*C12P 19/34*    (2006.01)
*C12Q 1/00*    (2006.01)
*C07H 21/04*    (2006.01)

(52) U.S. Cl. .............................. 435/91.2; 435/4; 435/6; 536/23.1; 536/23.7; 536/24.2; 536/24.3; 536/24.32; 536/24.33

(58) Field of Classification Search ..................... 435/4, 435/6, 91.2; 536/23.1, 23.7, 24.2, 24.3, 24.32, 536/24.33
See application file for complete search history.

*Primary Examiner*—Rodney P. Swartz
(74) *Attorney, Agent, or Firm*—Smith, Gambrell & Russell, LLP

(57) ABSTRACT

The present invention relates to detection of pathogenic mycobacteria in clinical specimens such as sputum, cerebrospinal fluid, gastric lavage and tissue biopsies etc., wherein the novel stretch of DNA that lies in the intergenic region between methyl mycolic acid synthase genes mmaA1 and mmaA2 and the flanking region in mmaA1 and mmaA2 genes and is the invention uses a pair of designed oligonucleotide primers that specifically amplifies the target DNA from the clinical specimens.

15 Claims, 7 Drawing Sheets

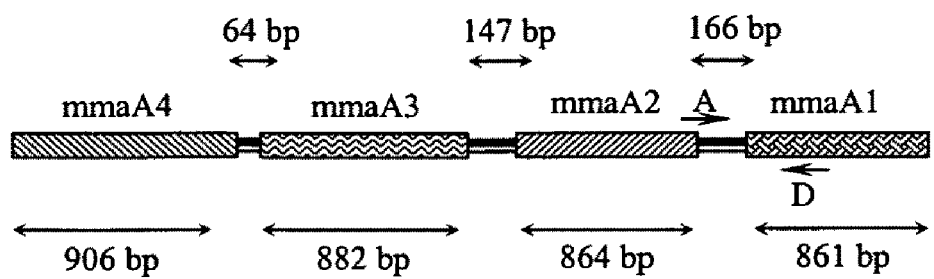
Fig. 1. Schematic diagram of methoxy mycolic acid synthase mmaA 4-mmaA 1 gene cluster of mycobacteria and location of forward A, and reverse D primers.

CTACTTCGCCAGCGTGAACTGGTTGACGTCGATGTAGCCGACCCGGAACAGCTTGGCGCAGCC
GGTCAGGTATTTCATGTACCGCTCGTAGACCTCTTCGGACTGGATCGCGATGGCCTCGCTTTTGTGTTC
CTGCAGCGCCTCGGCCCACAGGTCGAGGGTCCTGGCGTAATGCGGCTGCAGCGACTGGCGGCGAGTCA
GCGTGAAACCCGTCTTCGCCGACTGTTCCTCAACCATTTCAATCGTCGGAGGTTGGCCCCCCGGGAAG
ATTTCGGTCGCGATGAACTTGAGAAAGCGGGCCAGCCACAACGTGAGCGGCAAGCCGTGGTCGACCA
TCTGCTGCCTGGTCAGGCCGGTGATCGTGTGCAGCAGCAACACGCCATCGGGCGGCAGGATTTTGTGG
GCCCGGGCGAAGAAGTCGGCGTGACGATCGTGGCCGAAGTGCTCGAACGCGCCGATCGACACGATGC
GGTCGACGGGCTCGTTGAACTGCTCCCATCCCGCCAGCAACACTCGCCTGTCGCGCGGGGTGTCCATC
TCGTCGAACGACTTCTGCACATGGGCGGCCTGGTTCTTCGACAATGTCAGGCCGACGACGTTGACGTC
ATACTGCGCGATCGCGCGCCGCATGGTGGCGCCCCAGCCGCAACCGATATCGAGCAGCGTCATGCCGG
GCTGCAGACCTAGCTTGCCCAGCGCCAGGTCGATCTTGGCGATCTGGGCCTCTTCCAGCGTCATGTCCT
CGCGTTCGAAATGCGCGCAGCTGTAGGTCTGGGTCGGATCCAGGAACAGCCGGAAGAAGTCGTCGGA
CAGGTCGTAGTGTGCCTGCACGTCCTCGAAGTGCGGCGTTAGGTC*GTTGACCAT*gaggtgtaatgcctttccggaccct
aggtggcctttcggtgcttgcacggaacgcaccgatgcttcccctccccgcatgctcgaggcatgctatccgatacagggccgccgcactaaaccgcgatcgaatttgc
ccaggtcagggaacggatatgagcggacgagCTACTTGGTCATGGTGAACTGGGCGACGTTGATTAGGCCTCTGCGGAA
GCGCTCCGCGCATCCGGTCAGATAGTGCATGAAGTTGTTGTAGACCTCTTCGGACTGTACGGCGATGG
CGCGTTCGCGGGCAGCCTGTAGGTTGGCGGCCCATGCATC*GAGAGTCCGTGCGTAGTG*CTGCTGCAGCA
GCTGGACATGCTCGATGGTGAAGCCCGCGGCCTGCGCATTGTCGACAATGTCGGGCTCCGATGGCAGC
TCGCCGCCCGGGAAGATCGACTCCCGCAGGAATTTGAGGAATCGAAGGTCGCTCATCGTCAGCGCAAT
GCCCTGTTCGTGCAGCCACCTGCGGTCGTAGGTGAACAGGCTGTGCAGTAGCATCCGCCCGTCATCGG
GCAGGATGTCGTAGGAGCGTTCGAAGAACGTCAGATACCGCTCCTTTTTGAACGCGTCGAATGCCTCA
AAGCTGACGATCCGGTCGACGTTCTCTTCAAACTCTTCCCAGCCCTGCAGCCGGGCCTCGGCGCGCCGT
TGCGTTCCGATTGCGGCCAGGCGGTCTTTGCTGCGTTCATAGTGATTCCGGCTGAGCGTGAGGCCGATG
ACATTGACGTCGTACTTCTCCACGGCCCGAACGAGCGCCCCGCCCCACCCGCAACCCACGTCGAGTAG
CGTCATCCCCGGTTCGAGGTTCAGCTTGTCCAACGCCAGATCCACCTTGGCCAGTTGCGCCTCTTCCAG
CGTCATATCGTCACGCTCGAAATAGGCGCAGGTGTAGACCCAGGTGGGATCGAGGAACAACGCGAAG
AAGTCATCCGAAATGTCGTAAGCCGACTGTGACTCTTCGTAATATGGTCTCAGCTTGGCCAT Fig. 2. Sequence of mmaA2 and mmaA1 gene with an intergenic region of 166 base pair (shown in lower case. Location of forward A, sequence ID 1 and reverse primer D, sequence ID 2. Both primer sequences are underlined and italicized.

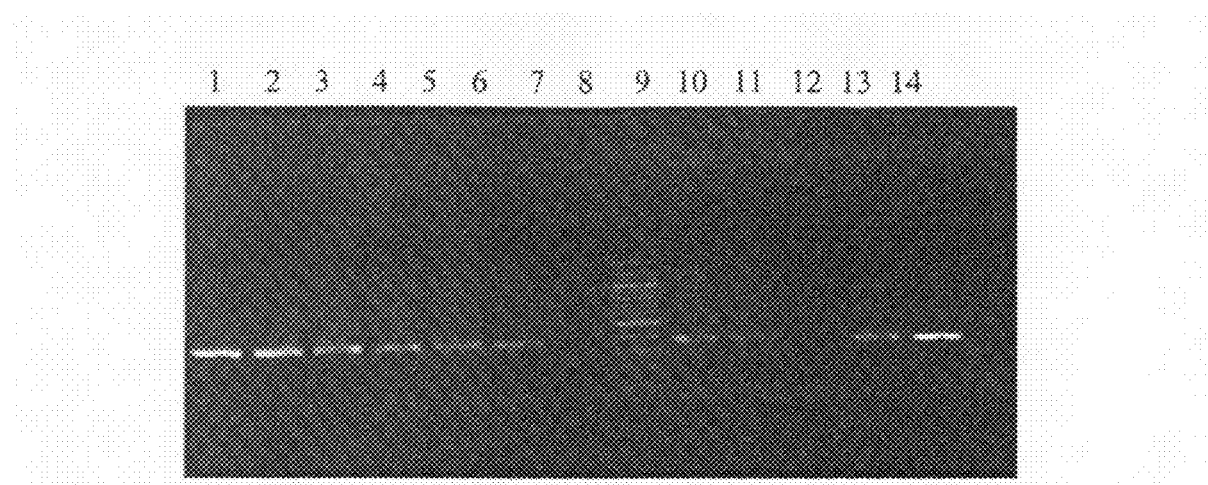
Fig. 3. PCR amplification of different mycobacterial genomic DNAs with primers A and D (lanes 1- 15): 1. *M.avium* 2. *M.bovis* 3. *M.chelonae* 4. *M.fortuitum* 5. *M.intracellulare* 6. *M.kansassi* 7. *M.phlei* 8. 100 bp DNA ladder 9. *M.marinum* 10. *M.scrofulaceum* 11.*M.smegmatis* 12. *M.szulgai*, 13. *M.tuberculosis* and 14. negative control. AD indicates 363 bp-amplified product.

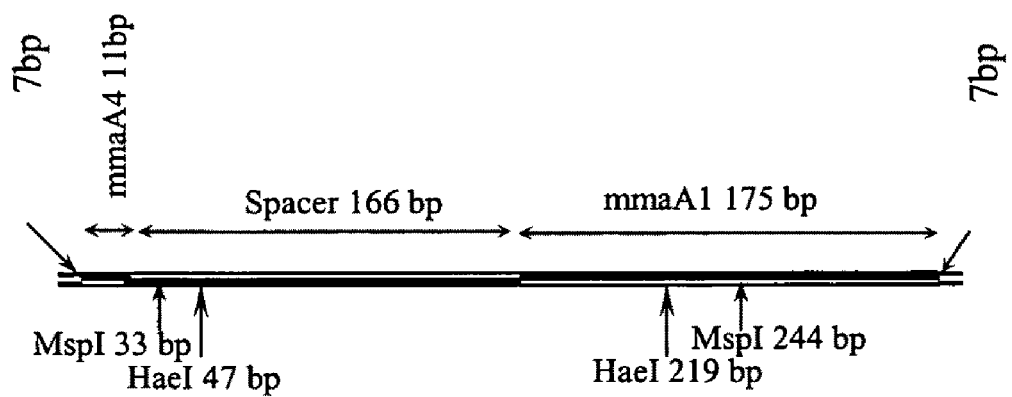
Fig. 4. Line diagram showing restriction endonuclease map of HaeI and MspI within AD.

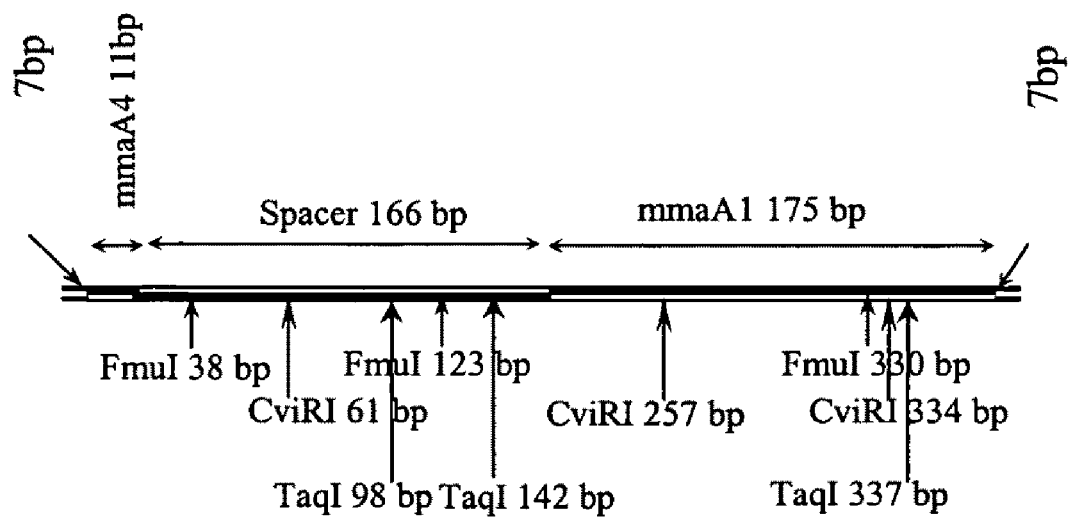
Fig. 5. Line diagram showing restriction endonuclease map of FmuI, CviRI and TaqI within AD.

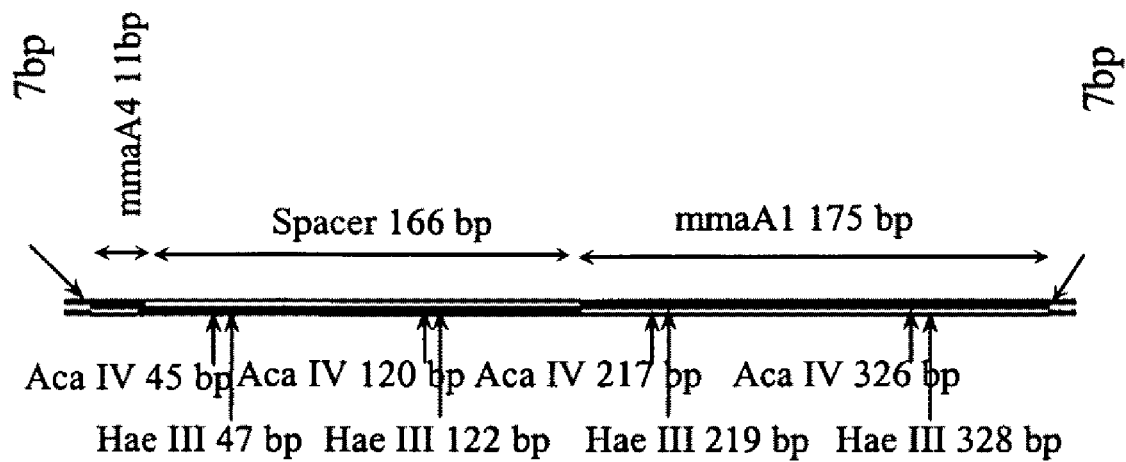
Fig. 6. Restriction map of AD showing distribution of the sites of restriction endonucleases AcaIV and HaeIII.

ARTICLE I
ARTICLE II
ARTICLE III
ARTICLE IV
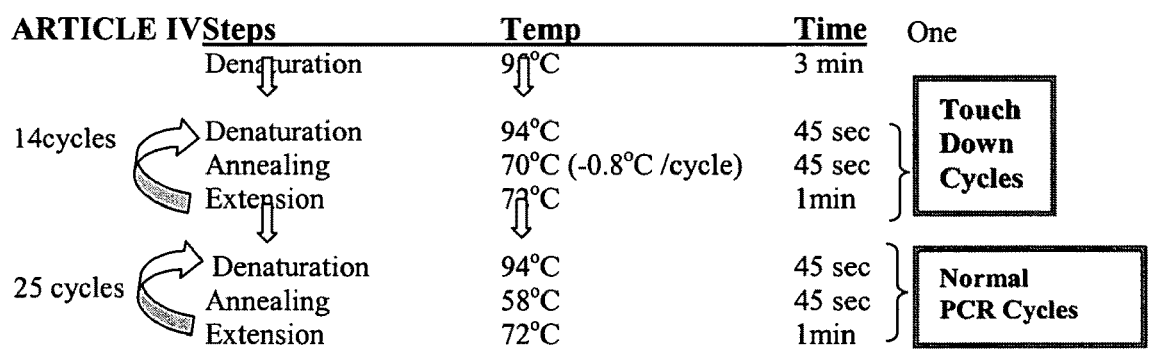
Fig. 7. Line diagram showing different steps of PCR reaction

METHOD FOR DETECTING PATHOGENIC MYCOBACTERIA IN CLINICAL SPECIMENS

FIELD OF THE INVENTION

The present invention relates to detection of pathogenic mycobacteria in clinical specimens such as sputum, cerebrospinal fluid, gastric lavage and tissue biopsies etc., wherein the novel stretch of DNA that lies in the intergenic region between methyl mycolic acid synthase genes mmaA1 and mmaA2 and the flanking region in mmaA1 and mmaA2 genes and is the invention uses a pair of designed oligonucleotide primers that specifically amplifies the target DNA from the clinical specimens.

BACKGROUND OF THE INVENTION

*Tuberculosis* is the number one killer disease. Every year it kills largest number of people due to a single infectious disease. According to a World Health Organization Report (WHO) over 8 million cases of tuberculosis are reported every year with over 2.9 million deaths

*Tuberculosis* deaths were gradually declining till early 90's by the virtue of availability of potent anti-tubercular drugs. The tuberculosis cases and deaths are again on rise mostly because of synergistic effect of co-infection with human immuno-deficiency virus (HIV)(Hopewell, P. C et al., 1992) and emergence of multiple drug resistant (MDR) strains of *M. tuberculosis* (Bloom, B. R, and C. L. Murray, 1992) and involvement of so called non tuberculous mycobacteria.

Over 70 species of mycobacteria are known, most are non-pathogenic for humans. *Tuberculosis* is caused by infection due to *M. tuberculosis*, with a few cases being caused by *M. bovis*. These organisms are genetically very close and called as *Mycobacterium tuberculosis* complex (MTC) organism. There is over a dozen other pathogenic mycobacteria, which causes tuberculosis like infection of lungs or other parts of the body. These organisms are called as mycobacteria other than tuberculosis (MOTT) or non-*tuberculous mycobacteria* (NTM). In the wake of AIDS epidemic these so called non *tuberculous mycobacteria* have become significant and are being isolated from large number of *tuberculosis* patients co-infected with HIV.

Early tuberculosis often goes unrecognized in an otherwise healthy individual. The lack of simple, rapid and reliable tests that can specifically detect *M. tuberculosis* and other causative agents in a clinical specimen poses enormous problems for both individual patient management and implementation of appropriate infection control and public health measures.

Classical methods of diagnosis include examination of a sputum smear under a microscope for acid-fast mycobactena and a X-ray of the lungs. However, in a vast majority of cases the sputum smear examination is negative for mycobacteria in the early stages of the disease, and lung changes may not be obvious on a X-ray until several months following infection. Staining of smear for acid-fast bacilli (AFB) takes less than two hours but lacks sensitivity and may be non-specific in some case. Moreover a positive result by AFB staining does not discriminate between the *mycobacterium* species.

Currently the only absolutely reliable method of diagnosis is based on culturing *M. tuberculosis* from the clinical specimen and identifying it morphologically and biochemically. Culturing of *M. tuberculosis* and other related organisms is sensitive and specific but is cumbersome and may take 6-12 weeks while culturing on solid media and three to six weeks on liquid media, during which time a patient may become seriously ill and infect other individuals. Therefore, a rapid test capable of reliably detecting the presence of *M. tuberculosis* is vital for the early detection, treatment and management of the patient.

Several molecular tests have been developed recently for the rapid detection and identification of *M. tuberculosis*. A commercial test, the Gen-Probe "Amplified *Mycobacterium Tuberculosis* Direct Test" has been evaluated by Abe et al and Miller et al. This test amplifies *M. tuberculosis* 16S ribosomal RNA from respiratory specimens and uses a chemiluminescent probe to detect the amplified product with a reported sensitivity of about 91%. Other commercial tests based on ligase chain reaction (LCR) (Abbott Laboratories), polymerase chain reaction (PCR) (Roche Diagnostics Systems, Eastman Kodak Co., Johnson & Johnson), Q-beta replicase (Gene Trak), and strand displacement amplification (Becton Dickinson).

Other methods based on immunological detection of infection with *M. tuberculosis* by non-culture methods are latex agglutination, radioimmunoassay and enzyme linked immunosorbent assays etc. Main drawback of these methods is their lack of sensitivity and or specificity (Kadival, et al., 1986; Yenez, et al., 1986). Serological techniques may be useful in some clinical settings but this approach is limited in general due to poor sensitivity and or specificity.

The development of polymerase chain reaction (PCR) (Saiki et al. 1988). that allows DNA to be amplified and detected from small amounts of nucleic acid samples has made it possible to detect *M. tuberculosis* specific nucleic acids in clinical specimens. Some of the earlier reports were based on the detection of the 16S ribosomal RNA or its gene. Detection of *M. tuberculosis* and related organisms by first amplifying a portion of DNA using a primer conserved for all bacteria then using species specific probes to detect different species of mycobacteria. Major drawback of this method is that this is cumbersome, and takes over 24 hours to complete. Species specific probes that are used to detect different species sequence in the amplified product vary only in few bases and subsequent analysis of this amplified DNA by assays based on hybridization, if carried out under less that ideal conditions can lead to a false positive test.

The discovery of the IS6110 insertion element (Thierry et. al. 1990) and the belief that this element may only be present in *M. tuberculosis* complex (*M. tuberculosis, M. bovis, M. africanum* and *M. microti*) spawned a whole series of rapid diagnostic strategies (Brisson-Noel et al., Clarridge et al., al., Forbes et al., Hermans et al., Kolk et al., Kox et al., Zambardi et al.). These tests employ various techniques to extract DNA from the sputum. PCR is used to amplify IS6110 DNA sequences from the extracted DNA. The successful amplification of this DNA is considered to be an indicator of the presence of *M. tuberculosis* infection. U.S. Pat. Nos. 5,168,039 and 5,370,998 has been issued to Crawford et al. for the IS6110 based detection of tuberculosis. Another U.S. Pat. No. 5,731,150 have been granted to CIBA CORNING DIAGNOSTICS CORP (Gurpreet. et.al). European patent EP 0,461,045 has been issued to Guesdon, J. L for the IS6110 based detection of tuberculosis. The IS6110 element was reported to be present at ten, two, one, five and five copies in *M. tuberculosis, M bovis, M. bovis* BCG, *M. africanum* and *M. microti* respectively. Most reports using IS6110 and other PCR based detection of tuberculosis claim sensitivities of over 75% and specificities approaching 100%.

A careful study on use of this sequence as a target for PCR based diagnosis of *M. tuberculosis* has reveled several drawbacks. A blind comparison study among 7 major laboratories authored by Noordhoek et al. raised a major concern when it reported false positive rates of 3 to 77% and sensitivities ranging from 2 to 90%. This study was significant because it allowed all participating laboratories to use their own detection strategies to identify IS6110, and the final results clearly indicate that existing protocols are severely deficient in terms of both sensitivity and specificity.

Another study by Lee et al. (1994) reported false positives of 62% while analyzing cerebrospinal fluid samples obtained from patients with tubercular meningitis. While specimen contamination from amplified IS6110 DNA originating from previously processed samples in the same laboratory may explain some false positives, this is not a major source of error because most laboratories maintain excellent specimen containment procedures to avoid contamination. This large number of false positive is because of the occurrence of IS6110 like sequences in organisms other than *M. tuberculosis*. IS6110 is a transposable insertion element (Calos and Miller), and these fragments of DNA have the property of being "mobile". IS6110 is also likely to have originated from (or been passed on to) other organisms, and certain regions of DNA may have remained conserved among these organisms during evolution. A report published by Mariani et al. also discusses the horizontal transfer between organisms of sequences related to the *M. tuberculosis* IS6110 element. This would explain some of the false positive tests reported in the literature. Additionally, Kent et al. were able to amplify sequences related to IS6110 from mycobacteria other than *M. tuberculosis*, confirming the suspicion that IS6110 like sequences were present in other organisms, and that they could be detected in a PCR carried out with IS6110 specific primers designed to detect *M. tuberculosis*. In order to address this issue, a systematic analysis of nucleic acid sequences deposited in GenBank was carried out and it was found stretches of sequences similar to IS6110 in organisms other than *M. tuberculosis*. Many of these organisms are found in clinical specimens.

Another fact which makes IS6110 an unsuitable target for the detection of tuberculosis is that some recent reports has showed that some *M. tuberculosis* isolates may altogether lack IS6110 sequence in its genome thus leading to false negative results. Studies on Asian isolates have reported that this sequence may be missing in at least some of the isolates (Yuen, L. K, et al. 1993) (Yuen, L. K. w. Ross. B. C, Jackson. K. M. and Dwyer. B. 1993. *J. Clin. Microbiol.* 31: 1615-1618.).

Another very important aspect of detection, differentiation and treatment of tuberculosis is the emergence of human immuno deficiency virus (HIV). Epidemiology and etiology of tuberculosis has undergone change since the rise of HIV, the causative agent for acquired immuno deficiency syndrome (ADS). Incidence of tuberculosis has increased considerably since the emergence of AIDS (Bafica, et al. 2003) Among AIDS deaths over 30% are due to *tuberculosis*. Since 1991 number of *tuberculosis* patients infected with HIV has increased from 3% to over 10%. Among AIDS patients only *M. tuberculosis* and *M. bovis* are not the only causative agents for tuberculosis. So called non-tuberculous mycobacteria have become significant pathogens in immunocompromised tuberculosis patients. Different laboratories have isolated other pathogenic mycobacteria called as non-tuberculous mycobacteria from clinical specimens derived from patients co-infected with HIV. Most important among them are *M. avium* and closely related group of mycobacteria i.e. *M. intracellulare* and *M. chelonae*. These organisms are known as *Mycobacterium avium-intracellulare* complex (MM complex) organisms. MAI complex of organisms presents symptoms that are indistinguishable from *tuberculosis*. They are responsible for pulmonary as well as disseminated form of disease in a large number of patients especially those infected with human immuno-deficiency virus (HIV). *M. avium* alone has been isolated from up to 30% of clinical specimens from pulmonary *tuberculosis* patients and at even higher number from disseminated *tuberculosis* patients. *M. kansasii* and *M. scrofulaceum* are other non-*tuberculous* mycobacteria that have been isolated from considerable number of AIDS patients with *tuberculosis*. Other non-*tuberculosis* mycobacteria are also being isolated from clinical specimen derived from AIDS patient. Reason for fewer isolation of non-*tuberculosis* mycobacteria may be non availability of simple, accurate and reliable tests to isolate and differentiate different types of non-*tuberculosis* mycobacteria. These findings suggest that the non-*tuberculosis* mycobacteria have become significant etiological agents in the wake of emergence of AIDS.

IS6110 is not specific for *M. tuberculosis* and may be absent in many isolates and other non-tubercular mycobacteria are the causative agent for tuberculosis especially in patients co-infected with HIV. It is clear from published reports that no existing technique based on IS6110 and other target sequence provides a level of confidence needed in a clinical diagnostic test.

This accentuates need for change in the approach of detection of tuberculosis. This calls for evaluation of new targets that are able to detect all pathogenic mycobacteria in a clinical specimen instead of detecting only *M. tuberculosis* complex group of organisms. Ideally there should be a diagnostic method that instead of detecting only *M. tuberculosis* complex group of bacteria should detect all pathogenic mycobacteria including non-tubercular mycobacteria in a clinical specimen. After detection of different pathogenic mycobacteria in a clinical specimen different types of pathogenic mycobacteria can be differentiated into different species of mycobacteria by PCR-RPLF method as described in this assay. Those patients infected with NTM alone or NTM together with *M. tuberculosis* complex group of organism will give a quick reference for possible co-infection with HIV and thus could be a good parameter to access HIV infection and spread in the population. Not many such tests are available that can detect pathogenic mycobacteria in a clinical specimens as well as differentiate them.

*Mycobacterium tuberculosis* Direct Test has been evaluated by Abe et al and Miller et al. This test amplifies *M. tuberculosis M. tuberculosis* 16S ribosomal RNA from respiratory specimens and uses a chemiluminescent probe to detect the amplified product with a reported sensitivity of about 91%. This test is complex, takes over 24 hours to complete and uses probes to identify different mycobacteria vary only in few bases which yields false positive result if done in even slightly less stringent condition.

Success of a PCR based assay depends on several factors. Most important among them are extraction of good quality nucleic acid amenable to PCR, design of a PCR primer specific for the pathogen and a PCR condition that can specifically amplify the target sequence from the isolated DNA.

A major weakness of currently available PCR based assays for detection of mycobacteria is the lack of a method of nucleic acid extraction that is simple, efficient and ensures safety to the user. Lysis of mycobacteria and purification of nucleic acid from clinical specimen without co-purifying impurities, which are known to be present in most clinical specimens, is a crucial step in a PCR based assay. A major drawback of the published protocols is that most methods used for extracting nucleic acids cannot be easily used for all types of specimens. Any nucleic acid extraction that necessitates a tedious and inefficient DNA purification will decrease the speed and sensitivity of the test. Additionally, having to carry out a different extraction procedure on different types of samples also makes the whole process expensive and slow. Operator safety is also a major concern when handling samples containing live *M. tuberculosis*. It was found that after careful analysis of different DNA extraction procedures described earlier that they were either highly inefficient or unable to remove impurities that are generally present in most clinical specimens (Boom, et. al. 1990) A simple, efficient and robust method of nucleic acid extraction from various clinical specimens was thus required to ensure sensitivity and reproducibility of a PCR based assay.

Specific and non-specific amplification of the target sequence is the another crucial factor in a success PCR based assay. At the slightest of sub-optimal condition even specific and unique primers can result into nonspecific amplification of the correctly sized band and thus may lead to false positive results (Gurpreet, S et,al). This has to be addressed in a practical and cost effective way.

OBJECTS OF THE INVENTION

Main object of the invention is to provide a method for detection of pathogenic mycobacteria in clinical specimens.

Another object of the invention relates to the design and composition of an assay to determine infection due to mycobacteria, by detecting a stretch of DNA by amplification of a portion of a gene cluster in various clinical specimen such as sputum, cerebrospinal fluid, gastric lavage, blood, bone marrow aspirates and tissue biopsies etc.

Yet another object of the invention relates to developing an efficient method of extracting DNA from all types of clinical specimens.

Still another object of the invention is to design a set of oligonucleotide primers capable of specifically amplifying a portion of a gene in a polymerase chain reaction.

Yet still another object of the invention is to a method of a polymerase chain reaction that allows specific amplification of the target.

Still another object of the invention is to provide a method to differentiate between various species of mycobacteria.

SUMMARY OF THE INVENTION

Present invention relates to detection of pathogenic mycobacteria in clinical specimens such as sputum, cerebrospinal fluid, gastric lavage and tissue biopsies etc. Novelties of the invention lie in novel stretch of DNA that lies in the intergenic region between methyl mycolic acid synthase genes mmaA1 and mmaA2 and the flanking region in mmaA1 and mmaA2 genes. This test uses a pair of oligonucleotide primers that specifically amplifies the target DNA from the clinical specimens. The invention describes a method of DNA extraction from clinical specimen, which is safer and yields more DNA from clinical specimens than the existing methods. Present invention also describes DNA amplification method that result in specific amplification of the target amplicon without use of expensive reagents thus making the test economical. Present invention elucidates a method for differentiation of different species of pathogenic mycobacteria in the clinical specimen by restriction fragment length polymorphism (RFLP) analysis of the amplified PCR product.

BRIEF DESCRIPTION OF THE ACCOMPANYING FIGURES/DRAWINGS

FIG. 1. Schematic diagram of methoxy mycolic acid synthase mmaA 4-mmaA 1 gene cluster of mycobacteria and location of forward A, and reverse D primers.

FIG. 2. Sequence of mmaA2 and mmaA1 gene with an intergenic region of 166 base pair (shown in lower case. Location of forward A, SEQ ID NO: 1 and reverse primer D, SEQ ID NO:2. Positions of both primer sequences are underlined.

FIG. 3. PCR amplification of different mycobacterial genomic DNAs with primers A and D (lanes 1-15); 1. *M. avium* 2. *M. bovis* 3. *M. chelonae* 4. *M. fortutitum* 5. *M. intracellulare* 6. *M. kansasii* 7. *M. phlei* 8. 100 bp DNA ladder 9. *M. marinum* 10. *M. scrofulaceum* 11. *M. smeginatis* 12. *M. szulgai* 13. *M. tuberculosis* and 14. negative control. AD indicates 363 bp-amplified product.

FIG. 4. Line diagram showing restriction endonuclease map of HaeI and MspI within AD.

FIG. 5. Line diagram showing restriction endonuclease map of FmuI, CviRI and Taq I within AD.

FIG. 6. Restriction map of AD showing distribution of the sites of restriction endonucleases AcaIV and HaeIII FIG. 7. Line diagram showing different steps of PCR reaction

DETAILED DESCRIPTION OF THE INVENTION

The objective of this work has been to develop a comprehensive technique that allow for rapid, safe and specific detection of tuberculosis causing mycobacteria. The limiting steps in any PCR based diagnosis are DNA extraction from clinical specimen, design of PCR primer that can specifically amplify target sequence and developing a PCR condition that will allow only specific amplification of the target sequence. A serious limitation of available tests is that they detect but could not differentiate various species of *mycobacteria*.

Various available protocols describe different methods of nucleic acid extraction and mix of reagents to lyse mycobacteria and purify nucleic acid from a clinical specimen. In various methods lysis is achieved by treatment of the specimen with alkalis, organic solvents, chaotropic agents, detergents or a mix of them. Several of the simpler methods claim to achieve the lysis by simple boiling in alkali, PCR buffer or even in plain water. Although these methods are simple and work generally well on pure culture, they are not so useful for a clinical specimen. The generally prevailing notion that PCR reaction is robust and the nucleic acid liberated by crude lysis methods can be used directly in a PCR reaction is not true. These methods are simple to use but often fail to kill all mycobacteria present in a clinical specimen and thus could be hazardous for the user. Such preparations are reported to contain many impurities that can easily inhibit a PCR reaction. It has been observed that such preparation may not result in amplification even on diluting the DNA several folds. The fact that extraction of clean DNA is of utmost importance for success of a PCR based assay.

The inventors have carefully optimized all steps in nucleic acid purification and developed a method that is simple, robust, and efficient and ensures complete safety for the operator. Further the treatment of the dirtier specimen like sputum by mild alkali and a mucolytic agent helps to remove many contaminating agents and results in cleaner nucleic acid preparation. This step also helps in removing other contaminating organisms present in dirtier samples like sputum and gastric lavage etc. Since sputum is the most commonly collected and submitted clinical specimen for pulmonary tuberculosis and is known to contain several contaminants that is potent inhibitor or PCR reaction, the modified lysis buffer developed in the prevent invention uses a strong chaotropic agent, ie, guanidinium isothiocyanate. This helps to inactivate all mycobacteria present in a clinical specimen, lyse tough mycobacterial cell and denature and remove proteins resulting into cleaner preparation of DNA (Table 3) and also ensures safety for the operator. By heating specimen in our lysis buffer even the toughest cells and objects like spores and baculovirus polyhedra are lysed easily. An earlier report by the same group has revealed use of guanidinium isothiocyanate for lysis and purification of nucleic from tough materials like baculovirus polyhedra and mycobacteria (Das et.al 1996) and (Bose. et al 1998).

TABLE 3

Serial Numbers one to three are samples prepared by described here while serial numbers four to six are sample prepared by the method of Gurpreet et.al.

| Sr. No | Dilution factor | OD at 260 nm | OD at 280 nm | 260/280 ratio | Concentration | purity |
|---|---|---|---|---|---|---|
| 1. | 50 | 0.011 | 0.019 | 1.82 | 27.60 µg/ml | No protein contamination |
| 2. | 50 | 0.010 | 0.017 | 1.85 | 25.00 µg/ml | No protein contamination |
| 3. | 50 | 0.013 | 0.024 | 1.88 | 33.03 µg/ml | No protein contamination |
| 4. | 50 | 0.006 | 0.011 | 1.62 | 17.13 µg/ml | protein contamination |
| 5. | 50 | 0.009 | 0.015 | 1.66 | 23.46 µg/ml | Protein contamination |
| 6. | 50 | 0.008 | 0.013 | 1.63 | 20.37 µg/ml | Protein contamination |

Another advantage of using this reagent is that most proteins are denatured in this buffer leading to through lysis of the mycobacteria present in the specimens. Other method also describe using this reagent (Gurpreet, et al. 1980). The present method is different from them in several ways. The lysis buffer in the present method has a composition that accomplishes more through lysis, does better deproteination and helps precipitate even minute amount of DNA. This results in cleaner DNA preparation with improved yield. Instead of using guanidinium isothiocyanate-tris-phenol for lysis the lysis buffer of the present invention contain detergent N lauryl sarcosyl, 200 mM NaCl and 10 mM 2' mercaptethanol together with 4M guanidinium isothiocyanate. Phenol being an extremely explosive and thus hazardous is not included in the lysis buffer. These modifications have made lysis buffer of the present invention complete and more potent. Detergent helps in solubilization of cell wall lipid and of protein and thus result in complete lysis of the mycobacterial cell wall, which is rich in different types of complex lipids. Use of NaCl helps in precipitation of nucleic acid present at minute amount and thus gives approximately 1.4-1.5 fold better DNA yield than the method described by Gurpreet et al. This is crucial especially when dealing with a clinical specimen which has fewer numbers of mycobacteria per ml of sample. Mycobacterial cells are inactivated and lysed by heating the digested and decontaminated sample in lysis buffer at 85° C. for 20 mill. This is safe, as compared to boiling as described in several methods is unnecessary and may result in popping of the cap or bursting of some tubes.

The lysate is extracted once with alkaline phenol. It has been noticed that deproteination by extraction with alkaline phenol is not unnecessary as claimed by many protocols. This simple step leads to removal of all proteins including the ones tightly bound to DNA and thus leads to cleaner nucleic acid preparation. This increases reproducibility of the assay especially when dealing with dirtier samples like sputum and gastric lavage. Nucleic acid is precipitated from the aqueous phase with equal volume of iso-propanol.

In the next step a set of oligonucleotide primer was designed that was specific for pathogenic mycobacteria. Care was taken to ensure that this sequence is absent in other pathogenic organisms or in human being since presence of such organisms and human cells cannot be ruled out in clinical specimens. A gene cluster mmaA1-mmaA4 accession numbers MTCY20H10.23c-MTCY20H10.26c of mycobacteria (FIG. 1) was employed for this purpose. This gene cluster contains four genes separated by three spacer regions of various lengths (FIG. 1). These genes methoxy-mycolic acid synthases are responsible for synthesis and modification of complex terminal mycolic acids present in pathogenic mycobacteria. These mycolic acids are implicated in pathogenicity of mycobacteria. Forward primer A, SEQ ID NO:3 is located from 1-9 bases in mmaA2 gene, 11 bp of this oligonucleotide primer lies in the 167 bp spacer region between the genes mmaA2 and mmaA1. Reverse primer D, SEQ ID NO:4 is located from 688-705 bases in the mmaA1 gene FIG. 1 and FIG. 2. These primer sequences were designed using the software Primer Select (Lasergene, DNASTAR) and do not show homology with sequences of organisms other than *M. tuberculosis* and *M. bovis*.

Another approach was also taken to ensure that this primer sequence is specific to pathogenic mycobactena. The oligonucleotide sequence was converted to amino acid (peptide) and compared of many pathogenic organisms and human using a software Genome Calculator developed at this institute (Institute for Genomics and Integrative Biology). This software converts a DNA sequence into amino acid (peptide) and compares it with all sequences available in the database by converting them into library of short peptides. This software found primer sequences to be specific to *M. tuberculosis* and *M. bovis* and not to be present in any of the 24 other pathogenic organisms or human whose whole genome sequence was available in the databases. PCR with the genomic DNA of all pathogenic mycobacterium tested resulted in amplification using these primers while PCR using the genomic DNA of non-pathogenic mycobacteria did not resulted in amplification FIG. 3 and Table 1.

TABLE 1

PCR amplification of AD from different pathogenic and non-pathogenic species of mycobacteria

| Mycobacterial Species | Strain | Pathogenic/nonpathogenic | PCR result |
|---|---|---|---|
| *M. avium* | ATCC | Pathogenic | positive |
| *M. bovis* | ATCC | Pathogenic | positive |
| *M. chelonae* | ATCC | Pathogenic | Positive |
| *M. fortuitum* | ATCC | Pathogenic | Positive |
| *M. intracellulare* | ATCC | Pathogenic | Positive |
| *M. kansasii* | ATCC | Pathogenic | Positive |
| *M. marinum* | ATCC | Pathogenic | Positive |
| *M. phlei* | ATCC | Non-pathogenic | Negative |
| *M. smegmatis* | ATCC | Non-pathogenic | Negative |
| *M. scrofulaceum* | ATCC | Pathogenic | Positive |
| *M. szulgai* | ATCC | Pathogenic | positive |

TABLE 1-continued

PCR amplification of AD from different pathogenic and non-pathogenic species of mycobacteria

| Mycobacterial Species | Strain | Pathogenic/nonpathogenic | PCR result |
|---|---|---|---|
| M. tuberculosis | ATCC | Pathogenic | positive |
| M. xenopi | ATCC | Pathogenic | positive |

After design of the specific primer next critical step was to design and develop a PCR condition that will specifically amplify only the desired target. This is crucial since PCR in sub-optimum condition result in nonspecific amplification of other stretch of DNA closely resembling the desired target in size Gurpreet et al. This in turn leads to less amplification of the desired target sequence and thus reduced specificity and sensitivity. Unlike the primers used by Gurpreet et, al. in their invention our primers do not result in amplification of a band of approximately same size from non-pathogenic mycobacteria even under sub optimal condition (FIG. 3).

Any nonspecific amplification is due to nonspecific annealing of oligonucleotide primers at the annealing step of the PCR. Most commonly adopted strategy to avoid nonspecific amplification is to do hot start PCR. This is achieved by adding a critical component of the reaction when the reaction is hot. For this purpose enzyme entrapped in wax beads are used or recently a new thermopolymerase enzyme (Thermopolymerase Gold, Perkin Elmer) has become available. This enzyme remains bound to monoclonal antibody raised against this enzyme and becomes active only when incubated at 95° C. for 10-15 min. However use of these measures make the test costlier by 10-20%.

Further the cycling conditions were modified which would discourage annealing of primer at sites other than desired. This was achieved if the initial few cycles of the PCR were undertaken at higher annealing temperature than the calculated melting temperature of the oligonucleotide primer and then gradually reduce annealing temperature in each cycle and do rest 25 cycles at the optimum annealing temperature. Once the specific amplicon is established in the initial cycles, they do not allow nonspecific products compete with them in the later cycles. This type of cycling condition is called as touch down PCR and helps specific amplification without use of expensive reagents. This measure helps to make the test more cost effective and easy to use.

Detection of the amplified PCR product is the next step in an assay. Amplified PCR product can be detected in several different ways. Electrophoresis on agarose or polyacrylamide gel is the most common and simple way of detecting an amplified PCR product. Use of agarose gel is simpler than polyacrylamide gel electrophoresis, or DNA ELISA, which is cumbersome, takes longer to detect and needs more expertise. Polyacrylamide gels are less sensitive as compared to agarose gels since polyacrylamide quenches the ethidium bromide dye used for detection. Besides, acrylamide is a potent neurotoxin and thus potentially hazardous for the user. A horizontal agarose gel electrophoresis method was used for resolution of PCR product. The amplified product is detected on a short wave UV transilluminator.

Recently labeling of the PCR product with biotin or a fluorescent dye or and subsequent detection of the product by ELISA has been described. This method can be easily adopted with any of the PCR based assay including ours.

This PCR based detection method not only meant for detection of different types of pathogenic mycobacteria in a clinical specimen but can be used to differentiate them in various species using the restriction fragment length polymorphism (RFLP) analysis of the PCR amplified fragment. RFLP is a very powerful tool for different species and strains of a species. It is based on the fact that each DNA has site for one or more restriction endonucleases. These sites are recognized precisely by class II restriction endonucleases derived from different bacteria. In natural course of evolution of an organism one or more of these sites are modified or lost. Therefore restriction with the same enzyme of a stretch of DNA results in polymorphism in the fragment length among different species of organisms and thus serve as an efficient tool for differentiation and epidemiology. AD is a suitable candidate for PCR-RFLP analysis of different species of mycobacteria since this stretch has portion of two genes has an intergenic region of 167 bp. This DNA stretch has two sites of several restriction endonucleases separated by several bases that will yield fragments in the size range that is suitable for analysis by polyacrylamide gel electrophoresis Table 2 (FIGS. 4, 5 and 6). These sites lie in intergenic as well as in the gene mmaA1 (FIGS. 4, 5 and 6). Restricted product can be easily separated on 10-12% polyacrylamide gel for RFLP mapping of different species. Presence of an intergenic region of 167 bp combined with well-laid out sites for some common restriction endonuclease make AD a suitable candidate for differentiation of different species of pathogenic mycobacteria by PCR-RFLP analysis.

TABLE 2

DNA stretch sites of several restriction endonucleases

| Enzyme | No. of Sites | Location | No. of fragments on restriction | Fragment Sizes |
|---|---|---|---|---|
| HaeI | 2 | 47 bp, 219 bp | 3 | 47 bp, 144 bp and 172 bp |
| Msp I | 2 | 33 bp, 244 bp | 3 | 33 bp, 119 bp and 211 bp |
| BsmNI | 3 | 74 bp, 239 bp and 333 bp | 4 | 30, 74, 94 and 165 bp |
| CviRI | 3 | 61, 257 and 334 bp | 4 | 29, 61, 77 and 196 bp |
| MwoI | 3 | 67, 237 and 331 bp | 4 | 32, 67, 94 and 170 bp |
| TaqI | 3 | 98, 142 and 337 bp | 4 | 26, 44, 98 and 195 bp |
| Aca IV | 4 | 45, 120, 217 and 326 bp | 5 | 37, 45, 75, 97 and 109 bp |
| HaeIII | 4 | 47, 122, 219 and 328 bp | 5 | 35, 47, 75, 97 and 109 bp |

The PCR reagents were made and dispensed in a clean room dedicated to PCR reagent preparation. No specimen, culture or purified DNA was ever introduced into the PCR mix room. Target DNA was added to the PCR mix in a separate room that has never been exposed to amplified DNA. Amplification was carried out in a MJ mini thermal cycler (M J Research) using 200-μl thin walled tubes with attached individual caps (Axygen). The first solution added to the PCR tube contained 2.0 μl of 10×PCR buffer (100 mM Tris.Cl pH 8.3, 500 mM KCl, 15 mM $MgCl_2$), 2.0 μl of dNTP mix (2.0 mM each of dATP, dGTP, dTTP and dCTP), 1.0 μl of primer SEQ ID NO: 5, 5 TGGATCCGTTGACCATGAGGTG-TAATG 3 (5 picomoles/μl), 1.0 μl of primer SEQ ID NO: 6, 5 GGAATTCCACTACGCACGGACTCTC 3 (5 picomoles/μl) and 0.2 μl Taq polymerase containing 1 unit of enzyme and 11.8 μl of water. The PCR tubes were taken to the sample preparation room and 2.0 μl of the DNA was added to it. The tubes were mixed well by tapping and were run on touch down PCR program (FIG. 7). This program had one initial denaturation at 95° C. for 3 min. Initial denaturation step was followed by 14 cycles of touch down containing one denaturation at 94° C. for 45 sec, one annealing beginning at 70° C. for 45 sec with a decrement of 0.8° C. in each touch down cycle and one extension at 72° C. for 1 mm. This was followed by 25 cycles of normal cycling containing one denaturation at 94° C. for 45 sec, one annealing at 58° C. for 45 sec and one extension at 72° C. for 1 mm. On completion of PCR the tubes were taken to another room for the analysis of amplified PCR product. 10 µl of the reaction was loaded on the 2.0% agarose gel, another 10 µl of the reaction was saved for PCR-RFLP analysis wherever required.

A total of 142 clinical specimens were used to evaluate this PCR-based assay for detection of pathogenic mycobacteria in clinical specimens. Of these 141 were sputum sample and one was cerebrospinal fluid.

Out of these 74 specimens that were positive by acid fast smear method, 68 were also positive by PCR. Four of them were positive by smear but negative by PCR. Smear result of all these patients had scanty report by acid fast microscopy. Besides duplicate samples from these patients were positive by PCR. Two specimens coming from the same patients were positive by smear but negative by PCR. Upon spiking of reaction containing DNA from these specimens with purified DNA these samples were found to contain inhibitors of PCR. These specimens were treated again with the lysis buffer and precipitated with iso-propanol yielded amplification. Thirty-one patients were negative by acid fast microscopy but positive by PCR. Clinical history of all these patients showed that they were positive for mycobacteria by smear method and were undergoing treatment and being smear negative was due to low bacillary load in these specimens. Remaining thirty-seven specimens were negative by both smear and PCR method. When their clinical report were examined they were found to be negative by other clinical parameters and had come to the hospital on the basis of preliminary symptoms like fever and cough.

Accordingly, the main the embodiment of the present invention relates to a method for detecting pathogenic mycobacteria in clinical specimens said method comprising steps of:
 (a) clarifying the clinical specimens from contaminant including mucus by conventional methods,
 (b) treating the processed clinical specimens obtained in step (a) with the modified lysis buffer to inactivate the live pathogenic mycobacteria to make the process safe for the user,
 (c) extracting genomic DNA from the processed clinical specimen obtained from step (b) using a modified method to increase the yield and quality of DNA,
 (d) designing sequence of SEQ ID No. 4 from the DNA obtained in step (c) for specific detection of pathogenic mycobacteria, said designed sequence comprising of selected intergenic region of SEQ ID No. 3, a flanking region containing a portion of the gene mmaA1 of SEQ ID No. 1 and a portion of gene mmaA2 of SEQ ID No. 2 of the DNA obtained in step (c),
 (e) designing and synthesizing a set of specific oligonucleotide primers of SEQ ID No. 5, which is the forward primer and SEQ ID No. 6, which is the reverse primer for Polymerase Chain Reaction (PCR) amplification of SEQ ID No. 4,
 (f) developing a PCR amplification process for specific amplification of SEQ ID No.4 of (d) said process comprising using the specific oligonucleotide primers designed and synthesized in step (e) for detecting presence of pathogenic mycobacteria in the clinical specimens and
 (g) analyzing the amplified PCR product by restriction fragment length polymorphism (RFLP) analysis for differentiation of the species of the pathogenic mycobacterium for a quick assessment of HIV co-infection.

Another embodiment of the present invention relates to SEQ ID No. 4, wherein said SEQ ID has the following sequence:

5' TGGATCCGTTGACCATGAGGTGTAATGCCTTTCCGGACCCTAGGTGGC

CTTTCGGTGCTTGCACGGAACGCACCGATGCTTCCCCCTCCCCGCATGCT

CGAGGCATGCTATCCGATACAGGGCCGCCGCACTAAACCGCGATCGAATT

TGCCCAGGTCAGGGAACGGATATGAGCGGACGAGCTACTTGGTCATGGTG

AACTGGGCGACGTTGATTAGGCCTCTGCGGAAGCGCTCCGCGCATCCGGT

CAGATAGTGCATGAAGTTGTTGTAGACCTCTTCGGACTGTACGGCGATGG

CGCGTTCGCGGGCAGCCTGTAGGTTGGCGGCCCATGCATCGAGAGTCCGT

GCGTAGTGGGAATTC 3'.

Yet another embodiment of the present invention relates to the clinical specimens selected from sputum, gastric lavage, cerebrospinal fluid, blood, tissue biopsies, or bone marrow aspirates and other body fluids or tissues.

Still another embodiment of the present invention relates to the clarification of specimen in the step (a) from the contaminants (live organisms other than mycobacteria and mucus) is carried out by digestion decontamination mix containing mild alkali, NaOH, tri sodium citrate and a mucolytic agent and guanidinium isothiocyanate in the range of about 0.4-2.5 M followed by concentrating the specimen by centrifugation.

One more embodiment of the present invention relates to the digestion decontamination mix containing mild alkali, NaOH, tri sodium citrate and a mucolytic agent and guanidinium isothiocyanate in the range of about 0.5-2.0 M Still another embodiment of the present invention relates to the embodiment wherein DNA in the step (c) is extracted from the treated clinical specimen using a modified lysis buffer by inclusion of ingredients comprising guanidinium isothiocyanate in a range of about 0.5-8 M, Tris.Cl pH 7.6 is in the range of about 20-100 mM, N lauryl Sarcosyl is in the range of about 0.5-2% by weight of the buffer, EDTA is in the range of about 0.1-20 mM, β-Mercaptoethanol is in the range of about 1-25 mM and NaCl is in the amount of about 0.2M and purifying the DNA to improve the yield by thorough precipitation by organic solvents.

Another embodiment of the present invention relates to the embodiment wherein guanidinium isothiocyanate is present at about 4 M, Tris.Cl pH 7.6 is present at about 50 mM, N lauryl Sarcosyl is present at about 1% by weight of the buffer, EDTA is present at about 1 mM, β-Mercaptoethanol is present at about 10 mM and NaCl is present at about 0.2M.

Still another embodiment of the present invention relates to the organic solvents wherein the organic solvents are selected from group comprising of phenol/chloroform mixture and chloroform One more embodiment of the present relates to the genomic DNA yield is increased in the range of about 25 to 50%.

In another embodiment of the present invention the genomic DNA yield is increased in the range of about 30 to 40%.

Yet another embodiment of the present invention relates to the modified lysis buffer wherein the modified lysis buffer provides a cleaner preparation of the DNA.

Another embodiment of the present invention relates to treatment wherein the treatment with the modified lysis buffer containing 4M guanidinium isothiocyanate inactivates the live mycobacteria to make the procedure safer for the operator.

Still another embodiment of the present invention relates to the high yielding amplification of DNA in step (f) is achieved by the modified Touch Down PCR cycling conditions said conditions comprising steps of initial high annealing temperature in the range of about 62-72° C. followed by lowering of temperature in the range of about 0.2-1° C. per PCR cycle for the first 10-25 cycles, which is the Touch Down step to an optimum annealing temperature of about 56-62° C. for another 30 PCR cycles.

One more embodiment of the present invention relates to high yield amplification of DNA is achieved by modified Touch Down PCR cycling conditions, said conditions comprising steps of initial high annealing temperature is about 70° C. followed by lowering temperature is about 0.8° C. per PCR cycle for about first 14 cycles to about 58° C. for another 25 PCR cycles.

In another embodiment, the present invention relates to the oligonucleotide primers capable of amplification of intergenic region of SEQ ID No. 4 for detection of pathogenic Mycobacteria in clinical specimens, these primers being selected from the group consisting of:
  a. 5' TGGATCCGTTGACCATGAGGTGTAATG 3' (SEQ ID No. 5), which is the forward primer, and
  b. 5' GGAATTCCACTACGCACGGACTCTC 3' (SEQ ID No. 6), which is the reverse primer.

One more embodiment of the present invention relates to the length of oligonucleotide primers wherein the length of oligonucleotide primers is between 5 and 100 bases.

Another embodiment of the present invention relates to the diagnostic kit for the detection of pathogenic mycobacteria in clinical specimens comprising primers selected from the group consisting of:
  (a) 5' TGGATCCGTTGACCATGAGGTGTAATG 3' (SEQ ID No. 5), which is forward primer, and
  (b) 5' GGAATTCCACTACGCACGGACTCTC 3' (SEQ ID No. 6). Which is the reverse primer The invention is illustrated by the following examples wherein the following samples are given by the way of illustration of the present invention and should not be construed to limit the scope of the present invention:

EXAMPLES

Example 1

Reagents

Trizma (Tris base), N-acetyl-L-Cysteine (NALC), Ethidium bromide, Agarose, K₂HPO4, KH₂PO4, Sodium Citrate, N lauryl Sarcosyl, EDTA, 2-Mercaptoethanol were purchased from Sigma Aldrich. USA.

Thermo-polymerase and dNTPs were obtained from New England Biolabs. USA.

Plasticwares were obtained from Axygen USA and Corning-Costar USA.

Example 2

Collection and Processing of Clinical Specimens

Clinical specimens 142 sputum and one cerebrospinal fluid were obtained from patients in sterile specimen bottles at Ramakrishna Mission Free *Tuberculosis* Clinic Karol Bagh, New Delhi, India. Samples were either processed immediately whenever possible or stored at 4° C. overnight before processing.

Sputum

Samples were processed by NALC—NaOH method. Approximately 1-3 ml Sputum was transferred to a 15 ml screw capped centrifuge tubes (Corming Costar Corp USA). To each sample added 1-3 ml of digestion decontamination buffer, mixed gently and let stand for 15 minutes at room temperature. Samples were diluted with 3 volumes of 0.67M phosphate buffer pH 6.8 and centrifuged at 3500 g for 15 min in a swing out rotor (Remi cetrifuge India). Sediments resuspended in 300 ul sterile distilled water. One third of the processed samples was used for culture wherever required and another two third for PCR. The portion earmarked for PCR was inactivated and lysed by adding 0.5 ml lysis buffer to the tubes and heating at 85° C. for 20 min.

Cerebrospinal Fluid

Cerebrospinal fluid (CSF) is considered to be generally sterile and does not need digestion and decontamination. 1-2 ml of cerebrospinal fluid (CSF) was transferred to a micro centrifuge tube (MCT) and spun at 12000 g for 3 minutes in a micro-centrifuge (Eppendorf, A. G Germany). The pellet was washed with 0.067M phosphate buffer pH 7.0 and resuspended in 300 μl sterile distilled water. Whole was used for PCR.

Example 3

Preparation of Smear

Acid-fast staining was done using basic fuschin dyes by staining procedure of Zeihl-Neelsen. From the mucoid part of sputum a small part was smeared in 1×2 cm. area. Smear was briefly heat fixed, flooded with basic fuschin dye and heated briefly over Bunsen burner. De-stained with acid alcohol 3% sulfuric acid in 95% ethanol. Slides were washed with distilled water and counter-stained with methylene blue (0.3% methylene blue chloride) for 1-2 minutes. Rinsed with water and air-dried. Slides were examined under oil immersion objective at 400× with a binocular microscope (Zeiss, Germany). Smear were scored as per WHO guidelines.

Example 4

Extraction of DNA from Processed Clinical Specimens Using Modified Lysis Buffer

A portion (200 μl) of digested and decontaminated sample was transferred to a micro centrifuge tube. To it 500 μl modified lysis buffer containing 4M guanidinium isothiocyanate, 50 mM Tris.Cl (pH 8.0), 1% N lauryl Sarcosyl, 1 mM EDTA, 10 mM 2-Mercaptoethanol and 0.2M NaCl was were added and mixed by inverting. Tubes were incubated at 85° C. with intermittent shaking for 20 mm to lyse the cells. To the lysate was added 200 μl 2.5M ammonium acetate pH 7.6, mixed by inverting. Mixture was spun at 12000 g for 5 minutes. Supernatant was once extracted with phenol and chloroform. DNA was precipitated with 0.8% by volume isopropyl alcohol. Pellet was washed thoroughly with 70% ethyl alcohol, briefly air-dried and dissolved in 30 µl TE buffer (10 mM Tris.Cl pH 8.3 and 0.01 mM EDTA pH 8.0). 2 µl of this was used for PCR amplification.

Example 5

Primer Design

Two oligonucleotide primers that amplify a portion of an essential gene of pathogenic mycobacterium were designed using Primer select software (DNASTAR software from LASERGENE INC). Methyl mycolic acid synthase is a cluster of four genes, mmaA1-mmaA4. These genes are involved in synthesis and modification of mycolic acids and is reported to be present only in pathogenic mycobacteria. 11 bp of forward primer lies in the intergenic region between mmaA1 and mmaA2 genes, while reverse primer is located in the methyl mycolic acid synthase 1 gene (mmaA1). These primers were checked for specificity to mycobacterium using the software GENOME CALCULATOR developed by Bio-informatics division at this Centre. Forward oligonucleotide primer, SEQ ID NO:5 is 27 bp long. Reverse primer SEQ ID NO:6 is 25 base pairs long. Forward primer A is located from 1-9 bases in mmaA2 gene, 11 bp of this oligonucleotide primer lies in the 167 bp spacer region between the genes mmaA2 and mmaA1. Reverse primer D, SEQ ID NO:2, is located from 688-705 bases in the mmaA1 gene FIGS. 1 and 2. Primer sequence has an overhang of seven base pairs at the 5' containing site for Bam HI restriction endonuclease. Oligonucleotide primer D also has a seven-bp overhang at the 5' end-containing site for EcoRI. These primers specifically amplify a 373 base pairs portion designated as Al) of an essential gene of pathogenic mycobacterium.

```
Forward primer
                                SEQ ID NO: 5
5' TGGATCCGTTGACCATGAGGTGTAATG 3'

Reverse Primer
                         Sequence ID number 6
5' GGAATTCCACTACGCACGGACTCTC 3'
```

Example 6

PCR Amplification of AD from DNA Isolated from Clinical Specimens

PCR reaction were carried out in 20 µl reaction volume containing 2.0 µl DNA from the above preparation, 50 mm KCl, 10 mM Tris.Cl pH 8.3, 1.5 mM MgCl$_2$ 10 pMoles of each oligonucleotide primers and 1 unit of thermo-polymerase. Reactions were carried out in duplicate second had a 2.0 µl of 10 fold dilution of the above DNA.

Several different cycling condition occurred to obtain clean PCR product without non-specific amplification. In the beginning a normal cycling condition occurred, containing one initial denaturation at 95° C. for 3 mm. followed by 30 cycles of one denaturation at 94° C. for 45 sec, one primer annealing at 60° C. for 45 sec and one extension at 72° C. for one minute. This was followed by a final extension at 72° C. for 5 minutes.

This was working well with purified DNA but was giving non-specific amplification with DNA isolated from clinical specimens. To overcome this a new polymerase chain reaction method was adopted.

Touch Down PCR

Touch down PCR method is an efficient method to eliminate non-specific amplification and thus improves yield and efficiency of a PCR reaction. In touch down the annealing of oligonucleotide primer slightly above than the determined (Temperature melting) Tm and the annealing Tm is reduced in each cycle till a desired annealing temperature is achieved. This measure does not allow establishment of non-specific product during the initial cycles and helps improve specific amplification as well as improves efficiency of PCR reaction many folds.

Cycling Conditions of Touch Down PCR

In this program, one initial denaturation at 95° C. for 3 mm was followed by 14 touch down cycles with one denaturation at 94° C. for 45 Sec, one annealing starting at 70° C. for 45 sec with 0.8° C. decrease in each cycle, one extension at 72° C. for 1 minute. Touch down was followed by 25 cycles with one denaturation at 94° C. for 45 Sec, one annealing at 58° C. for 45 Sec and one extension at 72° C. for 1 minute.

Example 7

Detection of Amplified PCR Products

Amplified PCR products were analyzed by electrophoresis on agarose gel. PCR reaction was mixed with 1.0 µl of 6× gel loading buffer and whole reaction was loaded on 1.8% agarose gel. Gels were prepared and run in 1×TAB buffer (0.04 M Tris-acetate and 0.001 M EDTA. After the electrophoresis, the gel was stained in the staining solution containing 0.5 µg/ml ethidium bromide. Gels were photographed and documented using Eagle eye gel documentation system (Stratagene).

ADVANTAGES OF THE PRESENT INVENTION

Several method of PCR based detection of mycobacteria in clinical specimens is available as described above. However each method has its own drawbacks and none of them is complete. The main drawback lies in isolation of DNA from clinical specimens. Clinical samples that come to the laboratory for detection contains several impurities that co purify with the DNA by most of the described methods and interfere with further steps of detection. Our method of DNA isolation removes the isolation and provides clean DNA for PCR. Another advantage of this method is selection of oligonucleotide primers for specific amplification of the target DNA stretch specific to pathogenic mycobacteria. A primer set was designed of which one of the primer lies in the intergenic region between an essential gene of mycobacteria while the other is located in an essential gene of mycobacteria. This primer pair is thus very unique to pathogenic mycobacteria and is able to specifically amplify a stretch of DNA from the pathogenic mycobacteria and not from other mycobacteria as is reported for many of the available primers. Other advantage of this method is that it does not use expensive reagents for PCR amplification of the target sequence in a stringent condition to achieve specific amplification as this increase the cost of the test. This method instead uses unique cycling condition to achieve specific amplification of the target DNA. So the cost of the test is reduced by approximately 10-20%. Another advantage of this method is because of the unique structure of the amplified DNA which contain an intergenic region and its flanking region falling in two essential genes of mycobacteria makes this an ideal target for restriction fragment length polymorphism (RFLP) based identification of different strains of pathogenic mycobacteria. Another advantage of this method is this method incorporates a step in the beginning of the test that inactivates pathogenic mycobacteria in the clinical specimens thus making the process safe for the user.

REFERENCES

Bafica A, Scanga C A, Schito M L, Hieny S, Sher A. 2003 J Immunol. August 1; 171(3): 1123-7
Bennedsen, J, Thomson, V. O, Pfyfer, G. E, Funke, J, Feldman, K, Beneke, A, Jenkins, P. A, Heginbothom, M., Fahr, A., Hengstler, M., Cleator, G., Clapper, P. and Wilkins, E. G. I. 1996. *J Clin. Microbiol.* 34: 1407-1411.
Boom, R. C. J. A. sol, M. M. salitnans, C. L. jansen, P. M. E. Wertheim-Van Dillen, and J. Van der Noorda. 1990. J. Clin. Microbiol. 28: 495-503.
Brisson-Noel, A., C. Aznar, C. Chureau, S. Nguyen, C. Pierre, M. Bartoli, R. Bonte, G. pialoux, B. Gicquel, and G. Garrigue. 1991. *Lancet* 338: 364-366.
Clarridge et al, Journal of Clinical Microbiology 31:2049-2056, 1993.
Daniel, T. M., and S. M. Debannne, 1987. *Am. Rev. Res. Dis.* 135: 1137-1151.
Eisenach, K. D., M. D. Cave, J, H. Bates and J. T. crawford. 1990 *J. Infect. Dis.* 161: 997-981
Hermans, P. W. M, A. R. J. Suchitema, D. V. Soolingen, C. P. H. J. Verstyner, E. M. Bik, J. E. R. Thole, A. H. J. Kolk, and J. D. A. V. Embden. 1990. *J. Clin. Microbiol.* 28: 1204-1213.
Kadival, G. V., T. B. M. S. Mazarelo. and S. D. Chaparas. 1986. *J. Clin. Microbiol.* 23: 901-904.
Kolk, A. H. J., A. R. J. Suchitema, S. Kuijper, J. Van Leewen, P. M. W. Hermans, J. D. A. Van Embden, and R. A. Hartskreel. 1992. *J. Clin. Microbiol.* 30: 2567-2575.
Kent et al, J. Clin. Microbiol. 33:2290-2293, 1995.
Kolk et al, J. Clin. Microbiol. 30:2567-2575, 1992.
Kox et al, J. Clin. Microbiol. 32:672-678, 1994.
Lee et al, J. Neurological Sciences 123:173-179, 1994.
Noordhoek, G. T., A. H. T. Kaan, S. Mulder, H. Wilke, and A. H. J. Kolk. 1995. *J. Clin. Pathol.* 48: 810-814.
Saiki, R. K., D. H. Gelfand, S. Stoffel, S. J. Scharf, R. Higuichi, G. T. Horn, K. B. Mullis and H. A. Erlich, 1988. *Science.* 239: 487-491.
Schirm., J., Oosendrop, L. A. B, and Mulder, J. G. 1995. *J. Clin. Microbiol.* 33: 3221-3224.
Thierry, D., A. Brisson-Noel, V. Levy-Frebault, S. Nguyen, J. Guesdon, and B. Gicquel. 1990. Thierry, D., Cave, M. D, Crawford, J. T, Bates, J. S, Gicquel, B. and Geusdon, J. L. 1989. *Nuc. Acid. Res.* 18: 188.
Yenez, M. A., M. P. Coppola, D. A. Russo, E. Delaha, S. D. Chaparas, and H. Yeager Jr. 1986. *J. Clin. Micobiol.* 23: 822-825.
Yuen, L. K. w., Ross, B. C, Jackson, K. M. and Dwyer, B. 1993. *J. Clin. Microbiol.* 31: 1615-1618.
Zambardi et al, Annales de Biologie Clinique 50:893-897, 1993.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

We claim:

1. A method for detecting pathogenic mycobacteria in a clinical specimen, said method comprising the steps of:
   (a) clarifying the clinical specimen from contaminant by conventional methods,
   (b) treating the processed clinical specimen obtained in step (a) with a lysis buffer comprising guanidinium isothiocyanate to inactivate live pathogenic mycobacteria to make the process safe for the user,
   (c) extracting genomic DNA from the processed clinical specimen obtained from step (b) using a buffer comprising sodium chloride to increase the yield and quality of DNA,
   (d) designing and synthesizing a set of specific oligonucleotide primers of SEQ ID NO: 5, which is the forward primer and SEQ ID NO: 6, which is the reverse primer,
   (e) PCR amplifying the genomic DNA from the processed clinical specimen to amplify the DNA stretch having SEQ ID NO: 4 using the specific oligonucleotide primers having SEQ ID NO: 5 and SEQ ID NO: 6, and
   (f) analyzing the amplified PCR product by restriction fragment length polymorphism (RFLP) analysis for differentiation of the species of the pathogenic mycobacterium for a quick assessment of HIV co-infection.

2. A method as claimed in claim 1, wherein the clinical specimen is selected from the group consisting of sputum, gastric lavage, cerebrospinal fluid, blood, tissue biopsies, bone marrow aspirates and other body fluids or tissues.

3. A method as claimed in claim 1, wherein clarification of the clinical specimen in step (a) from the contaminants is carried out by adding to said specimens a digestion decontamination mix containing mild alkali, NaOH, tri sodium citrate and a mucolytic agent and guanidinium isothiocyanate in the range of about 0.4-2.5 M followed by concentrating the specimens by centrifugation.

4. A method as claimed in claim 3, wherein the digestion decontamination mix contains mild alkali, NaOH, tri sodium citrate and a mucolytic agent and guanidinium isothiocyanate is in the range of about 0.5-2.0 M.

5. A method as claimed in claim 1, wherein the DNA in step (c) is extracted from the treated clinical specimen using a buffer comprising guanidinium isothiocyanate in a range of about 0.5-8 M, Tris.Cl pH 7.6 in a range of about 20-100 mM, N lauryl Sarcosyl in a range of about 0.5-2% by weight of the buffer, EDTA in a range of about 0.1-20 mM, β-Mercaptoethanol in a range of about 1-25 mM and NaCl is present in an amount of about 0.2M; and purifying the DNA to improve yield by thorough precipitation by organic solvents.

6. A method as claimed in claim 5, wherein guanidinium isothiocyanate is about 4M, Tris-HCl pH 7.6 is about 50 mM, N lauryl Sarcosyl is 100 by weight of the buffer, EDTA 1 mM, β-Mercaptoethanol is about 10 mM and NaCl is about 0.2M.

7. A method as claimed in claim 1, wherein the genomic DNA yield is increased 25 to 50%.

8. A method as claimed in claim 1, wherein amplification of DNA in step (e) is achieved by Touch Down PCR cycling conditions, said conditions comprising steps of providing an initial high annealing temperature in the range of 62-72° C. followed by lowering of temperature in the range of 0.1-1° C. per PCR cycle for the first 10-25 cycles, then subsequently carrying out 30 PCR cycles at an optimum annealing temperature of 56-62° C.

9. A method as claimed in claim 1, wherein amplification of DNA in step (e) is achieved by Touch Down PCR cycling conditions, said conditions comprising steps of providing an initial high annealing temperature of 70° C. followed by lowering of temperature of 0.8° C. per PCR cycle for about first 14 cycles to about 58° C. for another 25 PCR cycles.

10. A method as claimed in claim 1, wherein the forward primer is SEQ ID NO: 5 and the reverse primer is SEQ ID NO: 6.

11. A method as claimed in claim 1, wherein the length of oligomeric primers is between 5 and 100 bases.

12. A method as claimed in claim 1, wherein the lysis buffer provides a cleaner preparation of the DNA.

13. A method as claimed in claim 1, wherein treatment with the lysis buffer containing 4M guanidinium isothiocyanate inactivates the live mycobacteria to make the procedure safer for the operator.

14. A method as claimed in claim 1, wherein the contaminant clarified in step (a) comprises mucus and/or live organisms other than mycobacteria.

15. A set of primers
   consisting of SEQ ID NO: 5 and SEQ ID NO: 6.

* * * * *

SEQUENCE LISTING

<160> NUMBER OF SEQ ID NOS: 6

<210> SEQ ID NO 1
<211> LENGTH: 861
<212> TYPE: DNA
<213> ORGANISM: Mycobacterium tuberculosis

<400> SEQUENCE: 1

```
ctacttggtc atggtgaact gggcgacgtt gattaggcct ctgcggaagc gctccgcgca      60
tccggtcaga tagtgcatga agttgttgta gacctcttcg gactgtacgg cgatggcgcg     120
ttcgcgggca gcctgtaggt tggcggccca tgcatcgaga gtccgtgcgt agtgctgctg     180
cagcagctgg acatgctcga tggtgaagcc cgcggcctgc gcattgtcga caatgtcggg     240
ctccgatggc agctcgccgc ccgggaagat cgactcccgc aggaatttga ggaatcgaag     300
gtcgctcatc gtcagcgcaa tgccctgttc gtgcagccac ctgcggtcgt aggtgaacag     360
gctgtgcagt agcatccgcc cgtcatcggg caggatgtcg taggagcgtt cgaagaacgt     420
cagataccgc tccttttga acgcgtcgaa tgcctcaaag ctgacgatcc ggtcgacgtt     480
ctcttcaaac tcttcccagc cctgcagccg ggcctcggcg cgccgttgcg ttccgattgc     540
ggccaggcgg tcttttgctgc gttcatagtg attccggctg agcgtgaggc cgatgacatt     600
gacgtcgtac ttctccacgg cccgaacgag cgccccgccc cacccgcaac ccacgtcgag     660
```

-continued

```
tagcgtcatc cccggttcga ggttcagctt gtccaacgcc agatccacct tggccagttg    720
cgcctcttcc agcgtcatat cgtcacgctc gaaataggcg caggtgtaga cccaggtggg    780
atcgaggaac aacgcgaaga agtcatccga aatgtcgtaa gccgactgtg actcttcgta    840
atatggtctc agcttggcca t                                               861

<210> SEQ ID NO 2
<211> LENGTH: 864
<212> TYPE: DNA
<213> ORGANISM: Mycobacterium tuberculosis

<400> SEQUENCE: 2
ctacttcgcc agcgtgaact ggttgacgtc gatgtagccg acccggaaca gcttggcgca     60
gccggtcagg tatttcatgt accgctcgta gacctcttcg gactggatcg cgatggcctc    120
gcttttgtgt tcctgcagcg cctcggccca caggtcgagg gtcctggcgt aatgcggctg    180
cagcgactgg cggcgagtca gcgtgaaacc cgtcttcgcc gactgttcct caaccatttc    240
aatcgtcgga ggttggcccc ccgggaagat ttcggtcgcg atgaacttga gaaagcgggc    300
cagccacaac gtgagcggca agccgtggtc gaccatctgc tgcctggtca ggccggtgat    360
cgtgtgcagc agcaacacgc catcgggcgg caggattttg tgggcccggg cgaagaagtc    420
ggcgtgacga tcgtggccga agtgctcgaa cgcgccgatc gacacgatgc ggtcgacggg    480
ctcgttgaac tgctcccatc ccgccagcaa cactcgcctg tcgcgcgggg tgtccatctc    540
gtcgaacgac ttctgcacat gggcggcctg gttcttcgac aatgtcaggc cgacgacgtt    600
gacgtcatac tgcgcgatcg cgcgccgcat ggtggcgccc cagccgcaac cgatatcgag    660
cagcgtcatg ccgggctgca gacctagctt gcccagcgcc aggtcgatct tggcgatctg    720
ggcctcttcc agcgtcatgt cctcgcgttc gaaatgcgcg cagctgtagg tctgggtcgg    780
atccaggaac agccggaaga agtcgtcgga caggtcgtag tgtgcctgca cgtcctcgaa    840
gtgcggcgtt aggtcgttga ccat                                            864

<210> SEQ ID NO 3
<211> LENGTH: 166
<212> TYPE: DNA
<213> ORGANISM: Mycobacterium tuberculosis

<400> SEQUENCE: 3
gaggtgtaat gcctttccgg accctaggtg gcctttcggt gcttgcacgg aacgcaccga     60
tgcttccccc tccccgcatg ctcgaggcat gctatccgat acagggccgc cgcactaaac    120
cgcgatcgaa tttgcccagg tcagggaacg gatatgagcg gacgag                   166

<210> SEQ ID NO 4
<211> LENGTH: 363
<212> TYPE: DNA
<213> ORGANISM: Mycobacterium tuberculosis

<400> SEQUENCE: 4
tggatccgtt gaccatgagg tgtaatgcct ttccggaccc taggtggcct ttcggtgctt     60
gcacggaacg caccgatgct tccccctccc cgcatgctcg aggcatgcta tccgatacag    120
ggccgccgca ctaaaccgcg atcgaatttg cccaggtcag ggaacggata tgagcggacg    180
agctacttgg tcatggtgaa ctgggcgacg ttgattaggc ctctgcggaa gcgctccgcg    240
catccggtca gatagtgcat gaagttgttg tagacctctt cggactgtac ggcgatggcg    300
cgttcgcggg cagcctgtag gttggcggcc catgcatcga gagtccgtgc gtagtgggaa    360
```

```
-continued ttc                                                              363

<210> SEQ ID NO 5
<211> LENGTH: 27
<212> TYPE: DNA
<213> ORGANISM: Mycobacterium tuberculosis

<400> SEQUENCE: 5
tggatccgtt gaccatgagg tgtaatg                                     27

<210> SEQ ID NO 6
<211> LENGTH: 25
<212> TYPE: DNA
<213> ORGANISM: Mycobacterium tuberculosis

<400> SEQUENCE: 6
ggaattccac tacgcacgga ctctc                                       25
```